(12) United States Patent
Danner et al.

(10) Patent No.: US 9,079,149 B2
(45) Date of Patent: Jul. 14, 2015

(54) METHOD FOR PRODUCTION OF A MINISUSPOEMULSION OR SUSPENSION OF SUB-MICRON CORE/SHELL PARTICLES

(75) Inventors: Thomas Danner, Weinheim (DE);
Bernd Sachweh, Meckenheim (DE);
Sonja Viereck, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 658 days.

(21) Appl. No.: 12/514,915

(22) PCT Filed: Nov. 13, 2007

(86) PCT No.: PCT/EP2007/062266
§ 371 (c)(1),
(2), (4) Date: Jun. 24, 2009

(87) PCT Pub. No.: WO2008/058958
PCT Pub. Date: May 22, 2008

(65) Prior Publication Data
US 2010/0080898 A1    Apr. 1, 2010

(30) Foreign Application Priority Data

Nov. 14, 2006 (EP) .................................... 06124078
Feb. 6, 2007 (EP) .................................... 07101775

(51) Int. Cl.
*B01J 13/02* (2006.01)
*A61K 8/04* (2006.01)
(Continued)

(52) U.S. Cl.
CPC ................. *B01J 13/02* (2013.01); *A61K 8/044* (2013.01); *A61K 8/06* (2013.01); *A61Q 19/00* (2013.01)

(58) Field of Classification Search
USPC ............. 427/213.3–213.36; 428/402–402.24; 264/4–4.7
See application file for complete search history.

(56) References Cited

U.S. PATENT DOCUMENTS

| 4,421,660 A | 12/1983 | Solc Nee Hajna |
| 4,680,200 A * | 7/1987 | Solc .......................... 427/213.34 |

(Continued)

FOREIGN PATENT DOCUMENTS

| EP | 0 209 879 | 1/1987 |
| EP | 0 542 133 | 5/1993 |
| WO | 03 006151 | 1/2003 |

OTHER PUBLICATIONS

Hines et al., "Synthesis and Characterization of Strongly Luminescing ZnS-Capped CdSe Nanocrystals," J. Phys. Chem. 100:468 (1996).*

(Continued)

*Primary Examiner* — Randy Gulakowski
*Assistant Examiner* — Jeffrey Washville
(74) *Attorney, Agent, or Firm* — Oblon, McClelland, Maier & Neustadt, L.L.P.

(57) ABSTRACT

The proposal is made for a process for the preparation of a minisuspoemulsion of submicron core/shell particles, wherein
the starting material is a suspoemulsion of a first disperse liquid phase I in a second continuous liquid phase II, which
comprises, in the first disperse liquid phase I, submicron particles of a solid C forming the core, and
a precursor substance PS for the shell dissolved in molecularly disperse form and, if appropriate, a reactant R, and wherein
the submicron core/shell particles CS are prepared in the first disperse liquid phase I of the suspoemulsion by chemical or physical conversion of the precursor substance PS for the shell.

20 Claims, 3 Drawing Sheets

Figure 1:
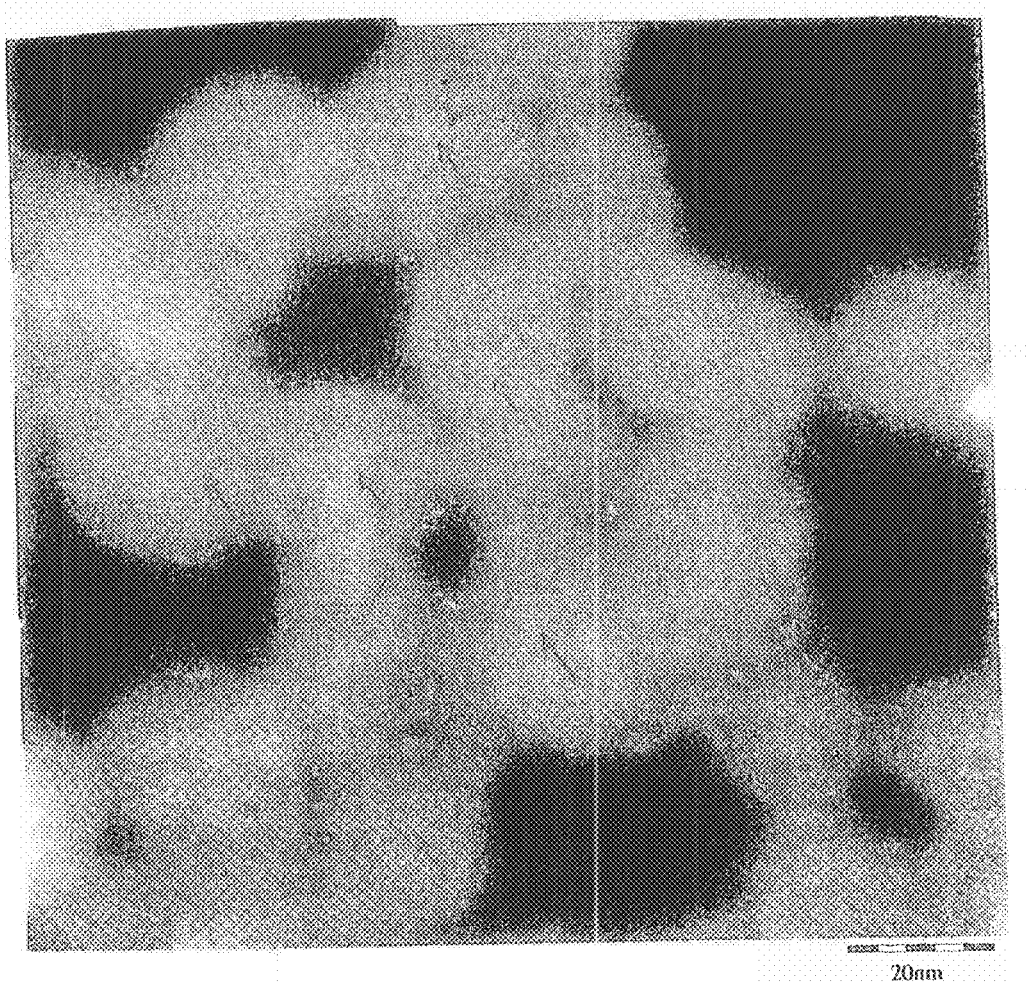

(51) Int. Cl.
*A61K 8/06* (2006.01)
*A61Q 19/00* (2006.01)

(56) References Cited

U.S. PATENT DOCUMENTS

2004/0254066 A1 12/2004 Ramarao et al.
2005/0129946 A1 6/2005 Hayashi
2006/0029802 A1* 2/2006 Ying et al. ................ 428/403
2007/0298337 A1 12/2007 Hayashi

OTHER PUBLICATIONS

U.S. Appl. No. 12/922,492, filed Nov. 12, 2010, Freidank, et al.

* cited by examiner

METHOD FOR PRODUCTION OF A MINISUSPOEMULSION OR SUSPENSION OF SUB-MICRON CORE/SHELL PARTICLES

The invention relates to a process for the preparation of a minisuspoemulsion or of a suspension of submicron core/shell particles.

Submicron core/shell particles are known and describe core/shell particles with a mean external diameter of less than 1 micrometer.

They are prepared in particular by flame synthesis, precipitation, for example in the centrifugal field, or by milling. For various applications, it is necessary to bring the submicron core/shell particles into suspension. For this, the submicron core/shell particles were hitherto first prepared according to one of the processes given above and, in the case of a pulverulent product, subsequently brought into suspension by addition of a liquid medium. It is a disadvantage that the submicron core/shell particles thus prepared tend to agglomerate, are poorly redispersible and exhibit a lack of long-term stability.

The term "suspensions" describes, in a known way, mixtures comprising a disperse solid phase in a continuous liquid phase.

The term "emulsions" describes liquid disperse systems which consist of two mutually immiscible liquid phases, the one phase of which, which is described as disperse or internal phase, is present dispersed in the form of fine droplets in the second phase, described as continuous or homogeneous phase. Depending on the polarity of the phases, emulsions are described as oil-in-water (O/W) or water-in-oil (W/O) emulsions, in the first case an oil phase, consisting of nonpolar media, being present in the form of finely dispersed drops in a polar phase consisting of an aqueous solution or other compounds immiscible with the nonpolar phase. In the case of the W/O emulsion, the polar phase is present the other way round in the form of finely dispersed drops in the oil phase. The proportion of the disperse phase to the whole of the emulsion can lie in a range from >0% to <100%.

The term "miniemulsion" is used for thermodynamically unstable liquid disperse systems (emulsions) stabilized kinetically by steric and/or electrostatic effects and/or by one or more surfactants and/or by additional auxiliaries, the disperse phase of which exhibits a mean droplet diameter ≤5000 nm (>5 µm).

The term "suspoemulsion" is used for mixtures exhibiting dispersed solid particles in an emulsion and corresponding as "minisuspoemulsion" a miniemulsion with dispersed solid particles therein.

A miniemulsion can be prepared, for example, by supplying mechanical energy, for example in the form of stirring energy, turbulent kinetic energy, ultrasound waves, pressure with subsequent relaxation via a homogenizing valve, by means of static mixers, micromixers or membranes or generally by impressing laminar or turbulent drag and/or extensional flows and cavitation. The type of emulsion (W/O emulsion or O/W emulsion) produced is determined by the choice of the material system of the disperse and continuous phases, of the surfactant or surfactants and/or of the auxiliaries used.

It is a precondition for the emulsification that the drops in the miniemulsion or in the suspoemulsion are sufficiently stable for the duration of the preparation of core/shell particles. This can be fulfilled, depending on material system, by surface charging, thus electrostatic repulsion, of the drops per se. Should external stabilizing of the drop phase by surfactants be necessary, this can be carried out via electrostatic and/or steric effects, caused by suitable stabilizing aids, or Pickering stabilizers (surface-active particles) present in the liquid continuous phase. Auxiliaries for stabilizing the particles and/or the emulsion may also be present in the liquid disperse phase. Auxiliaries for stabilizing the miniemulsion or the submicron suspension also include substances which change the rheological properties of the continuous phase in such a way that creaming or sedimentation of the drops or of the particles of the disperse phase are prevented or slowed down.

The term "liquid" is understood in the present case to mean phases which, under the conditions of the processes described in the present case, are in the liquid physical state.

It was an object of the invention to make available a process for the preparation of a minisuspoemulsion or of a suspension of submicron core/shell particles, according to which the shell can be applied in a specifically tailored fashion, in particular to all core particles in the same way, and which makes it possible to essentially retain the given polydispersity of the submicron starting suspension of one or more solids forming the core of the submicron core/shell particles and to make available submicron core/shell particles on an industrial scale in a quality comparable to the laboratory scale. The shell of the submicron core/shell particles can be open or closed, which is expressed in a covering closure index (occupied surface/core particle surface).

The object is achieved by a process for the preparation of a minisuspoemulsion or of a suspension of submicron core/shell particles, wherein the starting material is a suspoemulsion of a first disperse liquid phase I in a second continuous liquid phase II, which comprises, in the first disperse liquid phase I, submicron particles of a solid C forming the core, and a precursor substance PS for the shell dissolved in molecularly disperse form and, if appropriate, a reactant R, and wherein the submicron core/shell particles CS are prepared in the first disperse liquid phase I of the suspoemulsion by chemical or physical conversion of the precursor substance PS for the shell.

In the present case, the term "submicron particles of a solid C forming the core" is also understood to mean submicron particles of one or more solids C forming the core. By analogy, the term "a precursor substance PS for the shell dissolved in molecularly disperse form" is also understood to mean several precursor substances PS for the shell dissolved in molecularly disperse form and the term "a precursor substance PC for the core dissolved in molecularly disperse form" is also understood to mean several precursor substances PC for the core dissolved in molecularly disperse form.

It has been found that it is possible, in the drops of a first liquid phase I comprising both the one or the several solids forming the core and the one or the several precursor substances dissolved in molecularly disperse form of the solid forming the shell, to form the shell on the solid cores starting from the precursor substance dissolved in molecularly disperse forms. In this connection, the drops of the first liquid phase I, because of their small size (a minisuspoemulsion and, accordingly, as defined at the start, mean droplet diameters of the disperse phase ≤5 µm are concerned), operate as minireactors which guarantee that the given polydispersity of the submicron starting suspension of the solids forming the core is essentially retained.

The starting material for this is a suspoemulsion of a first disperse liquid phase I in a second continuous liquid phase II which comprises, in the first disperse liquid phase I, submicron particles of a solid C forming the core and a precursor substance PS for the shell dissolved in molecularly disperse form.

In one embodiment, the above suspoemulsion additionally comprises a reactant R.

The abovedescribed suspoemulsion can, in a first embodiment, be prepared by
  starting from a suspension of the submicron particles of the solid C forming the core in the first liquid phase I,
  adding the precursor substance PS for the shell thereto and dissolving in molecularly disperse form, and subsequently
  adding the second liquid phase II and emulsifying with the first liquid phase I while providing energy.

In an additional embodiment, the above suspoemulsion is prepared by
  starting from a suspoemulsion of submicron particles of a solid C forming the core in the first liquid phase I, as disperse phase, in the second liquid phase II, as continuous phase,
  introducing the precursor substance PS for the shell into a third liquid phase III which is miscible with the first liquid phase I but is immiscible with the second liquid phase II, and
  forming an emulsion from the third liquid phase III, comprising the precursor substance PS, with a fourth liquid phase IV, which is miscible with the second liquid phase II but immiscible with the first and the third liquid phase III, while supplying energy, and
  bringing the drops of the first liquid phase I and the drops of the third liquid phase III to coalescence by supplying energy.

In this embodiment, the disperse phase of a first suspoemulsion, comprising the submicron particles of the solid forming the core in the drops of the disperse phase, is accordingly brought to forced coalescence with the disperse phase of a second emulsion comprising the precursor substance PS for the shell in the drops of the disperse phase.

In an additional embodiment, the above suspoemulsion is made available which comprises, in the drops of the disperse phase, in addition to the submicron particles of the solid C forming the core and the precursor substance PS for the shell dissolved in molecularly disperse form, a reactant R. For this,
  the starting material is a suspoemulsion of submicron particles of a solid C forming the core and also a precursor substance PS for the shell dissolved in molecularly disperse form in the first liquid phase I, as disperse phase, in the second liquid phase II, as continuous phase,
  after which a reactant R either is added to the second continuous liquid phase II and diffuses into the drops of the first disperse liquid phase I or
  is added to an additional liquid phase V which is miscible with the first disperse liquid phase I but immiscible with the second continuous liquid phase II,
  an emulsion is formed from the additional liquid phase V, comprising the reactant R, with an additional liquid phase VI, while supplying energy, and the drops of the same
  are brought to forced coalescence with the drops of the first disperse liquid phase I comprising the solid C forming the core and also the precursor substance PS for the shell.

In an additional embodiment, the above suspoemulsion, comprising, in addition to the submicron particles of the solid C forming the core and the precursor substance PS for the shell dissolved in microdisperse form, the reactant R, is prepared by forced coalescence of the drops of a suspoemulsion, comprising the submicron particles of the solid C and the reactant R, with the drops of an additional emulsion, comprising, in the drops of the disperse phase, the precursor substance PS for the shell.

The preparation of the suspoemulsion comprising the submicron particles of the solid C forming the core in the first disperse liquid phase I, with the second liquid phase II as continuous phase, can take place analogously to the abovedescribed preparation process for the suspoemulsion comprising, in the drops of the disperse phase, the submicron solid particles C forming the core, the precursor substance PS for the shell dissolved in molecularly disperse form and, if appropriate, the reactant R. In a first embodiment,
  the starting material for this is a miniemulsion comprising a precursor substance PC for the solid forming the core in the first disperse liquid phase I, the second liquid phase II being the continuous phase, and the minisuspoemulsion of the solid C forming the core in the first disperse liquid phase I, with the second liquid phase II as continuous phase, being formed therefrom by physical or chemical conversion of the precursor substance PC of the solid forming the core.

In an additional embodiment,
  the starting material for this is a miniemulsion comprising a precursor substance PC for the solid forming the core in the first disperse liquid phase I, the second liquid phase II being the continuous phase,
  after which the reactant R either is added to the second continuous liquid phase II and diffuses into the drops of the first liquid phase I or
  is added to a third liquid phase III which is miscible with the first liquid phase I but is immiscible with the second liquid phase II, and
  an emulsion is formed from the third liquid phase III, comprising the reactant R, with a fourth liquid phase IV which is miscible with the second liquid phase II but immiscible with the first and the third liquid phase, while supplying energy, and is brought to forced coalescence with the drops of the first disperse liquid phase I comprising the precursor substance PC for the solid forming the core, and after which
  the precursor substance PC for the solid C forming the core is reacted chemically with the reactant R.

In the embodiment in which the submicron core/shell particles are prepared from the suspoemulsion comprising, in the drops of the disperse phase, the submicron particles of the solid C forming the core and also the precursor substance PS for the shell dissolved in molecularly disperse form by physical conversion of the precursor substance PS for the shell, the physical conversion can be triggered in particular by the change in one or more processing parameters, preferably the temperature and/or the pressure, or also by the addition of a solvent or a salt analogously to the abovedescribed addition of a reactant R. The physical conversion can in particular take place by cooling or by evaporation of the solvent of the dissolved solid or solids of the shell or of the core or through addition of an additional solvent analogously to the abovedescribed addition of a reactant R, which reduces the solubility of the dissolved solid or solids of the shell or of the core, or through addition of one or more additional salts analogously to the abovedescribed addition of a reactant R, which reduce the solubility of the dissolved solid or solids of the shell or of the core.

The term "submicron particles" describes, in a known way, solid particles having a mean external diameter of less than one micrometer. In particular, they can in this connection be nanoparticles having a mean external diameter in the nanometer range, in particular of less than 100 nm. The mean external diameter of the nanoparticles can preferably be ≥1 nm and ≤1000 nm, furthermore preferably ≥1 nm and ≤100 nm, in particular ≥1 nm and ≤20 nm. The thickness of the shell of the submicron core/shell particles can preferably lie in a range of ≥0.5 nm and ≤100 nm, furthermore preferably ≥0.5 nm and ≤30 nm, in particular ≥0.5 nm and ≤10 nm.

The particle size distribution can be determined in a way known per se, for example using the method of static light scattering or dynamic light scattering or an analytical ultracentrifuge (see, for example, W. Mächtle, Makromolekulare Chemie, 185 (1984), pages 1025 to 1039), but also from electron micrographs.

The submicron suspension comprises the solid or solids C forming the core preferably in a proportion of 0.01 to 40% by weight, in particular in a proportion of 1 to 10% by weight, based on the total weight of the submicron suspension.

The solid C forming the core or the solid S forming the shell can in particular be a substance or a mixture of substances chosen from the following list: metals, oxides, semiconductors, carbon blacks, metal salts, sulfur, sulfur compounds, silicon compounds, polymers, inorganic or organic pigments or solid inorganic or organic active substances for cosmetics, pesticides, animal nutritional agents or food supplements.

Preference is given in this connection to one or more metals chosen from the following list: Au, Ag, Ni, Pd, Fe, Sn, Zn, Co, Cu, Bi, Ce, Zr and Ti, or one or more oxides chosen from the following list: layered silicates, $TiO_2$, ZnO, $SiO_2$, $Bi_2O_3$, $Fe_2O_3$, $CeO_x$, $MFe_xO_y$, in which M is a transition metal or a main group metal, $ZrO_2$, SnO, $SnO_2$, $Al_xO_y$, CuO, $Cu_2O$ and $CaCO_3$, or one or more semiconductors chosen from sulfides and selenides, or silicon compounds, or metal salts chosen from nitrates, carbides, carbonates, sulfates, halides, acetates, salts of organic acids, such as lactates or carboxylates, carbonic acids, hydroxy acids or polymers chosen from PET, polyacrylonitrile, polystyrene, polyketone, polycarbonate, PMMA, PU or polybutadiene terephthalate. Use is preferably made, as molecularly disperse precursor substance PS of the solid S forming the shell or as precursor substance PC of the solid C forming the core, of one or more organic or inorganic salts, in particular tin salts, zinc salts, cerium salts, iron salts, zirconium salts, bismuth salts or copper salts, or inorganic metal compounds, in particular of titanium, monomers and/or one or more silicon compounds.

The reactant can be a base soluble in organic compounds, in particular an amine, or a water-soluble base, such as an aqueous sodium hydroxide or potassium hydroxide solution, or also a gas, such as carbon dioxide or ammonia, a reducing agent ($H_2$, $NaBH_4$), an oxidizing agent, initiators, a buffer solution or ion-exchange resins.

One of the two mutually immiscible liquids is hydrophilic and the other hydrophobic.

Preferably, the first disperse liquid phase I is aqueous and the second continuous liquid phase II is an organic phase (in particular an alkane or a mixture of alkanes, a vegetable oil or a mixture of vegetable oils, a silicone oil or a mixture of silicone oils, or a mixture of the listed substances).

In an alternative embodiment, it is possible, starting from the minisuspoemulsion of the submicron core/shell particles, by drawing off the first disperse liquid phase I or the second continuous liquid phase II, to obtain a suspension of submicron core/shell particles in the other liquid phase each time.

In an advantageous alternative embodiment, it is possible for two or more, in particular from 2 to 1000, of the particles forming the core to be enveloped together by one shell. "Multicore particles" are thereby obtained. In this connection, the shell does not have to be completely closed.

It is accordingly possible, per drop of the first disperse liquid phase I, to comprise several multicore particles, depending on the precipitation conditions, which can be better controlled in the drops of the first disperse liquid phase with sizes in the nanometer range than in bulk synthesis.

In an additional alternative embodiment, it is possible for all the particles forming the core, which are present in a drop of the first disperse liquid phase I, to be enveloped together by one shell. Since all drops have essentially the same size and comprise essentially the same concentration of core particles, it is possible in this embodiment to definitively adjust, via the concentration of the core particles and the size of the drops, the size of the multicore particles obtained, and multicore particles with a very uniform distribution width are obtained.

Advantageously, two to ten, preferably two to three, shells can be applied one above the other to the particles forming the core.

In an advantageous embodiment, the core and the one or the more shells may each exhibit an identical chemical composition but a different modification, in particular a different crystal structure, or the material of the core may be amorphous and the material of the one or the more shells may be crystalline, or vice versa.

In an additional embodiment, a minisuspoemulsion of submicron core/shell particles is prepared in which the shell does not completely enclose the core, after which the submicron core/shell particles are subjected to a downstream processing stage in which the core is completely or partially removed, in particular by evaporation, dissolution or corrosion, while preserving a hollow structure, and subsequently an additional shell or several additional shells can preferably be applied to the same.

The special fields of establishment of the core/shell nanoparticle suspensions or suspoemulsions obtained according to the process according to the invention depend on the chemical composition of the submicron core/shell particles, on the stabilizing aids used and on the substances forming the liquid phase I, the liquid phase II or the liquid phases I and II. Preferred fields of application are as catalysts, as active substance formulation, in particular in cosmetics, pesticides, animal nutritional agents or food supplements, as pigments, in electronics, in optical applications or in polymers.

The invention is more fully explained below with the aid of exemplary embodiments.

EXAMPLE 1

The starting material was the suspension of a first disperse liquid phase I comprising silicon dioxide particles, surface-modified with aminopropyltrimethoxysilane, with a mean particle size of 20 nm in water, Quadrol L® from BASF AG, i.e. tetrahydroxypropylethylenediamine, CAS No. 102-60-3, as surfactant and tin(II) chloride. The suspoemulsion comprised the first disperse liquid phase I in a second continuous liquid phase of n-decane and Glissopal EM23® from BASF AG and a surfactant of a zwitterionic molecule based on polyisobutene with the average molar mass of approximately 1000 g/mol.

The first disperse liquid phase was prepared by dissolving 0.75 g of the surfactant Quadrol L® and 2.25 g of tin(II) chloride in 96 g of water with stirring. Subsequently, 0.75 g of surface-modified silicon dioxide particles was added.

The second continuous liquid phase was prepared by dissolving 4.5 g of Glissopal EM23® in 199 g of n-decane with stirring.

The first disperse liquid phase and the second continuous liquid phase were preemulsified in an Ultra-Turrax® mixing device from IKA®-Werke GmbH & Co. KG (Staufen, Germany). Subsequently, the crude suspoemulsion thus prepared was degassed by establishment of vacuum.

This crude suspoemulsion was emulsified in a high-pressure homogenizer so that a drop size distribution with a Sauter mean diameter $x_{3,2}$ of 530 nm appeared. Subsequently, this fine emulsion was degassed by establishment of vacuum.

5.63 g of pyridine were added to this fine emulsion so that the pyridine dissolved in the continuous phase of the suspoemulsion. Subsequently, heating was carried out to 120° C. and this temperature was maintained for 4 hours.

In this way, particles with a core-shell structure could be prepared. Tin dioxide was deposited as 5 nm particles on the surface of the silicon dioxide core particles.

All liquids were separated from the minisuspoemulsion of submicron core/shell particles thus obtained in order to be able to take a High Angle Annular Dark Field-Scanning-Transmission Electron Microscopy photograph (HAADF-STEM photograph).

The HAADF-STEM photograph shows that, in the core-shell particles, the particle size of the core particles and also the polydispersity of the core particles have not essentially changed.

EXAMPLE 2

Use was likewise made, as core particles, of silicon dioxide particles surface-modified with aminopropyltrimethoxysilane but differing from example 1 with a mean particle size of 150 nm.

In order to prepare the suspension of the first disperse liquid phase I of the future suspoemulsion, 1.5 g of tin(II) chloride were dissolved in 64 g of water and subsequently 0.5 g of surface-modified silicon dioxide particles with a mean particle size of 150 nm was added.

The second continuous liquid phase was prepared by dissolving 3 g of Glissopal® EM23 from BASF AG in 133 g of n-decane.

The first disperse phase and the second continuous phase were preemulsified in an Ultra-Turrax® mixer from IKA®-Werke GmbH & Co. KG (Staufen, Germany). Subsequently, the crude suspoemulsion thus prepared was degassed by establishment of vacuum.

This crude suspoemulsion was emulsified in a high-pressure homogenizer so that a drop size distribution with a Sauter mean diameter $x_{32}$ of 350 nm appeared. Subsequently, this fine emulsion was degassed by establishment of vacuum.

4.8 g of triethylamine were added to the fine emulsion so that this base dissolved in the continuous phase of the suspoemulsion. Subsequently, heating was carried out to 130° C. and this temperature was maintained for 4 hours.

Particles with a core/shell structure were obtained, tin dioxide being deposited as 5 nm particles on the surface of the silicon dioxide core particles.

As in example 1, all liquids were separated off in order to be able to take a HAADF-STEM photograph.

The HAADF-STEM photograph shows that the particle size of the core particles and also the polydispersity of the core particles have not been essentially changed by application of the shell.

EXAMPLE 3

The starting material was the suspension of a first disperse liquid phase I comprising silicon dioxide particles, surface-modified with aminopropyltrimethoxysilane, with a mean particle size of 40 nm in water and tin(II) chloride. The suspoemulsion comprised the first disperse liquid phase I in a second continuous liquid phase of n-decane and Glissopal EM23® from BASF AG and a surfactant of a zwitterionic molecule based on polyisobutene with the average molar mass of approximately 1000 g/mol.

The first disperse liquid phase was prepared by dissolving 0.64 g of tin(II) chloride in 63 g of water with stirring. Subsequently, 0.2 g of surface-modified silicon dioxide particles was added.

The second continuous liquid phase was prepared by dissolving 3 g of Glissopal EM23® in 133 g of n-decane with stirring.

The first disperse liquid phase and the second continuous liquid phase were preemulsified in an Ultra-Turrax® mixing device from IKA®-Werke GmbH & Co. KG (Staufen, Germany). Subsequently, the crude suspoemulsion thus prepared was degassed by establishment of vacuum.

This crude suspoemulsion was emulsified in a high-pressure homogenizer so that a drop size distribution with a Sauter mean diameter $x_{3,2}$ of 580 nm appeared. Subsequently, this fine emulsion was degassed by establishment of vacuum.

2.05 g of triethylamine were added to this fine emulsion so that the triethylamine dissolved in the continuous phase of the suspoemulsion. Subsequently, heating was carried out to 130° C. and this temperature was maintained for 4 hours.

In this way, it was possible for core/shell particles with a multicore/shell structure to be prepared. Tin monoxide was deposited as shell on the surface of several silicon dioxide particles. It was possible, from an EDX analysis (energy dispersive X-ray analysis), to estimate the mean number of silicon dioxide particles per multicore/shell structure as approximately 6 silicon dioxide particles.

All liquids were separated off from the minisuspoemulsion of submicron multicore/shell particles thus obtained in order to be able to take a transmission electron microscopy photograph (TEM photograph), more specifically a TEM bright field image.

Figure 3:
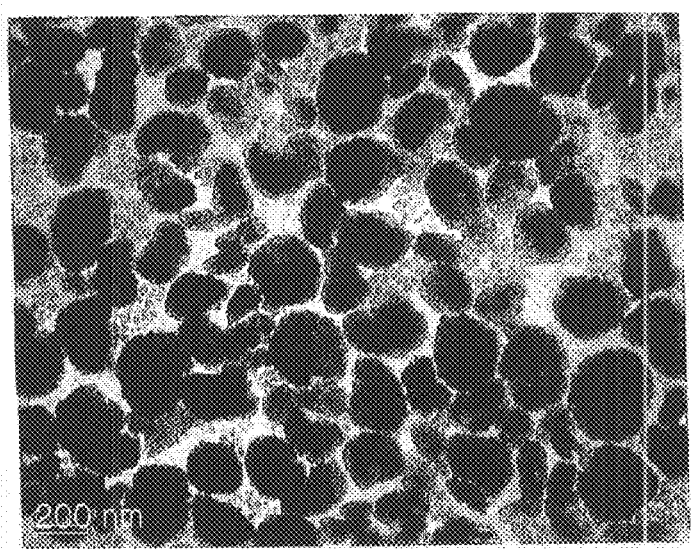

The TEM bright field image in FIG. 3 shows that the multicore/shell particles prepared all lie in the same order of magnitude.

Figure 2:
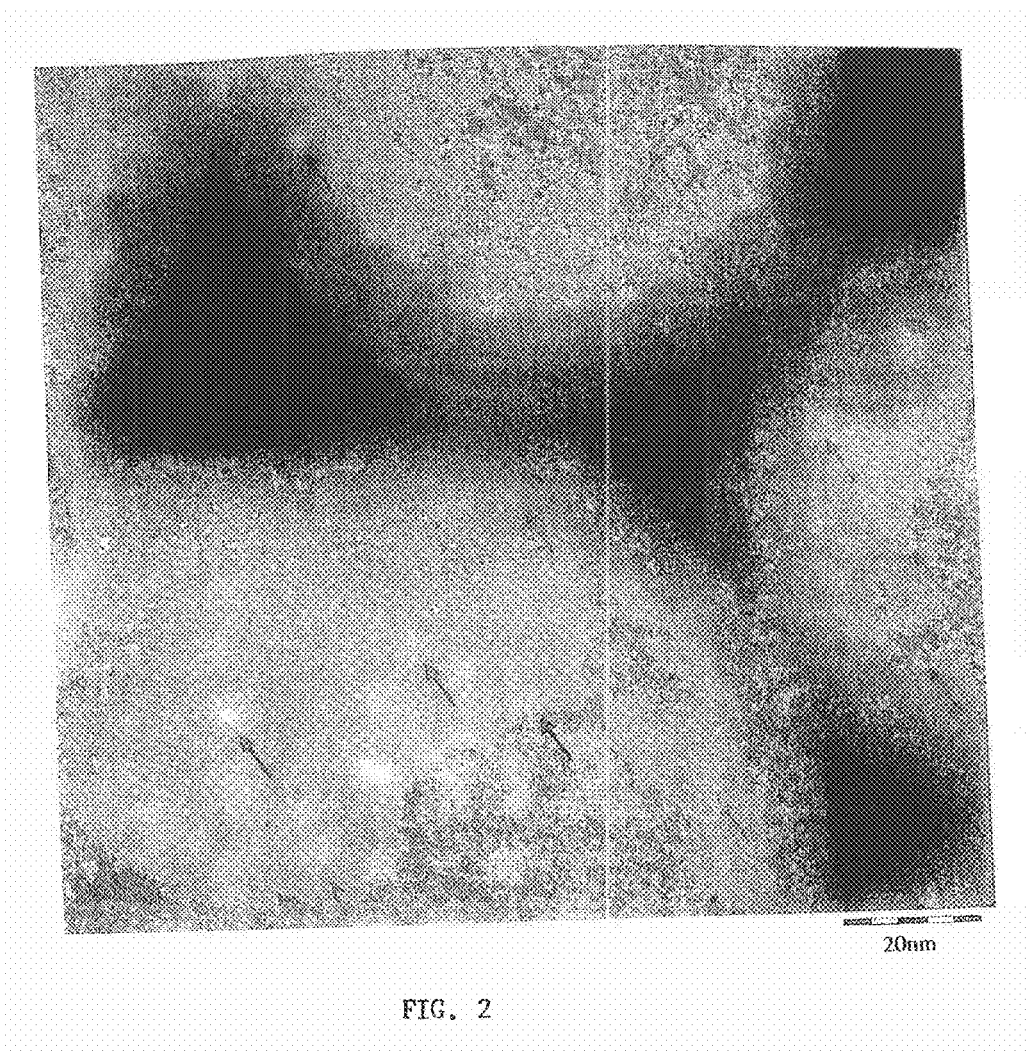

In the depiction:

FIG. 1 shows in detail a HAADF-STEM image of the core/shell nanoparticles obtained according to exemplary embodiment 1, FIG. 2 shows in detail a HAADF-STEM image of the core/shell nanoparticles obtained according to exemplary embodiment 2 and FIG. 3 shows in detail a TEM bright field image of the core/shell particles with a multicore/shell structure obtained according to exemplary embodiment 3.

Constituents of higher order and comparatively thicker sites on the specimen are marked out darker in the TEM bright field images (FIG. 3) and brighter in the HAADF-STEM images (FIGS. 1 and 2).

The HAADF-STEM photographs in FIG. 1 and FIG. 2 show that core/shell nanoparticles were obtained with a mean particle diameter in the same order of magnitude as the core particles used as starting material in the preparation.

The bright regions highlighted with the arrows in FIG. 1 and FIG. 2 show the tin dioxide particles which form the shell of the core/shell nanoparticles.

The TEM bright field image in FIG. 3 shows a multitude of core/shell particles with a multicore/shell structure, the darker structures in the TEM bright field image corresponding to the tin oxide particles forming the shell.

The exemplary embodiments accordingly clearly show that the shell formation on the core particles produced beforehand takes place very uniformly and each individual core particle carries a shell with approximately the same thickness. The process can be scaled up in a simple way because the mean drop diameter of the disperse phase is adjustable independently of the amount of the suspoemulsion in the same size, the mean drop diameter of the disperse phase defining the size of the minireactors which guarantee that the given polydispersity of the submicron starting suspension of the solids forming the core is essentially retained in the product, the core/shell particles.

What is claimed is:

1. A process for the preparation of a minisuspoemulsion of submicron core/shell particles CS, wherein the starting material is a minisuspoemulsion of a first disperse liquid phase I in a second continuous liquid phase II, said process comprising:
adding submicron core-forming particles C to said first disperse liquid phase I,
dissolving, in a molecularly disperse manner, a precursor substance PS for the shell S and, optionally, a reactant R, in the first disperse liquid phase I containing the submicron core-forming particles C, and then
emulsifying said first disperse liquid I containing the submicron core-forming particles C and the precursor substance PS and, optionally, a reactant R, in said second continuous liquid phase II, thereby forming at least one shell S about the surfaces of the core-forming particles C,
wherein said emulsifying occurs by supplying energy in the form of turbulent kinetic energy, in the form of ultrasound waves, by a static mixer, by a micromixer, by impressing laminar drag in the presence of a membrane, by impressing laminar extensional flow in the presence of a membrane, by impressing turbulent drag in the presence of a membrane, or by impressing turbulent extensional flow in the presence of a membrane,
wherein the first disperse liquid phase I is in the form of droplets comprising the submicron core-forming particles C for forming the core and the precursor substance PS for forming the shell S dissolved in a molecularly disperse form, wherein the droplets have a mean droplet diameter of $\leq 5$ μm, and
wherein two to ten shells S surround the core, each shell S present on top of the previous shell S.

2. The process according to claim 1, further comprising
introducing the precursor substance PS into a third liquid phase III prior to said dissolving;
emulsifying the third liquid phase III with a fourth liquid phase IV while supplying energy; and
coalescing the first liquid phase I in the form of drops with the third liquid phase III in the form of drops while supplying energy,
wherein said third liquid phase III is miscible with said first liquid phase I but immiscible with said second liquid phase II, and said fourth liquid phase IV is miscible with the second liquid phase II but immiscible with the first liquid phase I.

3. The process according to claim 1, further comprising
adding said reactant R to said second continuous phase II prior to said dissolving to diffuse reactant R into drops of the first disperse liquid phase I.

4. The process according to claim 1, further comprising
adding said reactant R to an additional liquid phase V prior to said dissolving;
emulsifying said additional liquid phase V with a second additional phase VI while supplying energy to form an additional emulsion;
coalescing said first disperse phase I in the form of drops with said additional emulsion in the form of drops while supplying energy,
wherein said additional liquid phase V is miscible with the first disperse liquid phase I but immiscible with the second continuous liquid phase II.

5. The process according to claim 1, further comprising
adding said reactant R to a third liquid phase III prior to said dissolving;
emulsifying said third liquid phase III with a fourth liquid phase IV while supplying energy;
coalescing said first disperse phase I in the form of drops with the third liquid phase III in the form of drops by supplying energy; and thereafter
adding the precursor substance PS to the second continuous phase II to thereby diffuse the precursor substance PS into drops of the first disperse liquid phase,
wherein said third liquid phase III is miscible with the first liquid phase I but immiscible with the second liquid phase II.

6. The process according to claim 1, further comprising
adding said reactant R to a third liquid phase III prior to said dissolving;
emulsifying said third liquid phase III with a fourth liquid phase IV while supplying energy;
coalescing said first disperse phase I in the form of drops with the third liquid phase III in the form of drops by supplying energy; thereafter
adding the precursor substance PS in the form of an additional emulsion to said first liquid disperse phase I, and thereafter
coalescing said first disperse liquid phase I in the form of drops with said liquid phase of said additional emulsion in the form of drops,
wherein said third liquid phase III is miscible with the first liquid phase I but immiscible with the second liquid phase II, a disperse phase of said additional emulsion is miscible with the first disperse liquid phase I but immiscible with the continuous liquid phase II and a continuous phase of said additional emulsion is miscible with the first continuous phase II.

7. The process according to claim 1, further comprising
removing the first disperse liquid phase I or the second continuous phase II to form a suspension of submicron core/shell particles CS in the second continuous phase II.

8. The process according to claim 1, further comprising
removing the second continuous phase II to form a suspension of submicron core/shell particles CS in the first disperse liquid phase I.

9. The process according to claim 1, wherein at least two particles forming the core C are surrounded by one shell S.

10. The process according to claim 1, further comprising removing the core from the core/shell particles CS for particles where the shell does not completely surround the core thereby forming a hollow structure.

11. The process according to claim 1, wherein at least one of a salt and a solvent is present with said reactant R.

12. The process according to claim 1, wherein the submicron core-forming particles C is at least one member selected from the group consisting of a metal, an oxide, a semiconductor, carbon black, a metal salt, sulfur, a sulfur compound, a silicon compound, a polymer, an inorganic pigment, an organic pigment, a solid inorganic substance active for cosmetics, a solid organic substance active for cosmetics, a pesticide, an animal nutrition agent, and a food supplement.

13. The process according to claim 1, wherein the precursor substance PS is at least one member selected from the group consisting of a metal, an oxide, a semiconductor, carbon black, a metal salt, sulfur, a sulfur compound, a silicon compound, a polymer, an inorganic pigment, an organic pigment, a solid inorganic substance active for cosmetics, a solid organic substance active for cosmetics, a pesticide, an animal nutrition agent, and a food supplement.

14. The process according to claim 1, wherein the submicron core-forming particles C is at least one member selected from the group consisting of a tin salt, a zinc salt, a cerium salt, an iron salt, a zirconium salt, a bismuth salt, a copper salt, a titanium compound, and at least one silicon compound.

15. The process according to claim 1, wherein the precursor substance PS is at least one member selected from the group consisting of a tin salt, a zinc salt, a cerium salt, an iron salt, a zirconium salt, a bismuth salt, a copper salt, a titanium compound, and at least one silicon compound.

16. A process for the preparation of a minisuspoemulsion of submicron core/shell particles CS, wherein the starting material is a minisuspoemulsion of a first disperse liquid phase I in a second continuous liquid phase II, said process comprising:
  adding submicron core-forming particles C to said first disperse liquid phase I,
  dissolving, in a molecularly disperse manner, a precursor substance PS for the shell S and, optionally, a reactant R, in the first disperse liquid phase I containing the submicron core-forming particles C, and then
  emulsifying said first disperse liquid I containing the submicron core-forming particles C and the precursor substance PS and, optionally, a reactant R, in said second continuous liquid phase II, thereby forming at least one shell S about the surfaces of the core-forming particles C,
  wherein said emulsifying occurs by supplying energy in the form of turbulent kinetic energy, in the form of ultrasound waves, by a static mixer, by a micromixer, by impressing laminar drag in the presence of a membrane, by impressing laminar extensional flow in the presence of a membrane, by impressing turbulent drag in the presence of a membrane, or by impressing turbulent extensional flow in the presence of a membrane,
  wherein the first disperse liquid phase I is in the form of droplets comprising the submicron core-forming particles C for forming the core and the precursor substance PS for forming the shell S dissolved in a molecularly disperse form, wherein the droplets have a mean droplet diameter of $\leq 5$ μm, and
  further comprising removing the core from the core/shell particles CS for particles where the shell does not completely surround the core thereby forming a hollow structure.

17. The process of claim 16, further comprising
  introducing the precursor substance PS into a third liquid phase III prior to said dissolving;
  emulsifying the third liquid phase III with a fourth liquid phase IV while supplying energy; and
  coalescing the first liquid phase I in the form of drops with the third liquid phase III in the form of drops while supplying energy,
  wherein said third liquid phase III is miscible with said first liquid phase I but immiscible with said second liquid phase II, and said fourth liquid phase IV is miscible with the second liquid phase II but immiscible with the first liquid phase I.

18. The process of claim 16, further comprising
  adding said reactant R to said second continuous phase II prior to said dissolving to diffuse reactant R into drops of the first disperse liquid phase I.

19. The process of claim 16, further comprising
  adding said reactant R to an additional liquid phase V prior to said dissolving;
  emulsifying said additional liquid phase V with a second additional phase VI while supplying energy to form an additional emulsion;
  coalescing said first disperse phase I in the form of drops with said additional emulsion in the form of drops while supplying energy,
  wherein said additional liquid phase V is miscible with the first disperse liquid phase I but immiscible with the second continuous liquid phase II.

20. The process of claim 1, further comprising
  adding said reactant R to a third liquid phase III prior to said dissolving;
  emulsifying said third liquid phase III with a fourth liquid phase IV while supplying energy;
  coalescing said first disperse phase I in the form of drops with the third liquid phase III in the form of drops by supplying energy; and thereafter
  adding the precursor substance PS to the second continuous phase II to thereby diffuse the precursor substance PS into drops of the first disperse liquid phase,
  wherein said third liquid phase III is miscible with the first liquid phase I but immiscible with the second liquid phase II.

* * * * *